US009357318B2

(12) United States Patent
Case et al.

(10) Patent No.: US 9,357,318 B2
(45) Date of Patent: May 31, 2016

(54) HEARING PROSTHESIS WITH ACCESSORY DETECTION

(71) Applicant: Cochlear Limited, Macquarie University (AU)

(72) Inventors: Alexander Case, Macquarie University (AU); Rami Banna, Macquarie University (AU); David Thambiratnam, Macquarie University (AU); Felicity Allen, Edmonton (CA)

(73) Assignee: Cochlear Limited, Macquarie University (AU)

( * ) Notice: Subject to any disclaimer, the term of this patent is extended or adjusted under 35 U.S.C. 154(b) by 103 days.

(21) Appl. No.: 14/194,061

(22) Filed: Feb. 28, 2014

(65) Prior Publication Data

US 2014/0296619 A1 Oct. 2, 2014

Related U.S. Application Data

(63) Continuation of application No. 13/249,969, filed on Sep. 30, 2011, now Pat. No. 8,706,245.

(51) Int. Cl.
*A61N 1/36* (2006.01)
*H04R 25/00* (2006.01)

(52) U.S. Cl.
CPC .......... *H04R 25/606* (2013.01); *A61N 1/36032* (2013.01); *H04R 25/43* (2013.01); *H04R 25/305* (2013.01); *H04R 2225/61* (2013.01)

(58) Field of Classification Search
CPC .. H04R 25/43; H04R 25/305; H04R 2225/41; H04R 2225/59; H04R 2225/61; A61N 1/36032
See application file for complete search history.

(56) References Cited

U.S. PATENT DOCUMENTS

| 4,467,145 | A | 8/1984 | Borstel |
| 5,824,022 | A | 10/1998 | Zilberman et al. |
| 7,319,768 | B2 | 1/2008 | van Oerle |
| 8,706,245 | B2 * | 4/2014 | Case ..................... H04R 25/43 607/55 |
| 2003/0059076 | A1 | 3/2003 | Martin |

* cited by examiner

*Primary Examiner* — George Evanisko
(74) *Attorney, Agent, or Firm* — McDonnell Boehnen Hulbert & Berghoff LLP

(57) ABSTRACT

The present application discloses hearing prostheses with two modes of operation and methods for operating the prostheses. In the first mode of operation, a hearing prosthesis receives a microphone input and produces an output based on the microphone input. In the second mode of operation, the hearing prosthesis may detect an accessory input signal and switch to an accessory input mode. The second mode of operation may produce an output that is based at least in part on the accessory input signal. Some embodiments may include detecting an accessory input signal with a detector. In response to detecting an accessory input signal, the hearing prosthesis may switch to an accessory operation mode. When the accessory input signal is not detected, the hearing prosthesis may operate in microphone operation mode.

18 Claims, 5 Drawing Sheets

HEARING PROSTHESIS WITH ACCESSORY DETECTION

CROSS-REFERENCE TO RELATED APPLICATIONS

This is a continuation of U.S. patent application Ser. No. 13/249,969 filed on Sep. 30, 2011, the contents of which are hereby incorporated by reference.

BACKGROUND

Various types of hearing prostheses may provide persons with different types of hearing loss with the ability to perceive sound. Hearing loss may be conductive, sensorineural, or some combination of both conductive and sensorineural hearing loss. Conductive hearing loss typically results from a dysfunction in any of the mechanisms that ordinarily conduct sound waves through the outer ear, the eardrum, or the bones of the middle ear. Sensorineural hearing loss typically results from a dysfunction in the inner ear, including the cochlea where sound vibrations are converted into neural signals, or any other part of the ear, auditory nerve, or brain that may process the neural signals.

Persons with some forms of conductive hearing loss may benefit from hearing prostheses, such as acoustic hearing aids or vibration-based hearing aids. An acoustic hearing aid typically includes a small microphone to detect sound, an amplifier to amplify certain portions of the detected sound, and a small speaker to transmit the amplified sounds into the person's ear. Vibration-based hearing aids typically include a small microphone to detect sound, and a vibration mechanism to apply vibrations corresponding to the detected sound to a person's bone, thereby causing vibrations in the person's inner ear, thus bypassing the person's auditory canal and middle ear. Vibration-based hearing aids may include bone anchored hearing aids, direct acoustic cochlear stimulation devices, or other vibration-based devices. A bone anchored hearing aid typically utilizes a surgically-implanted mechanism to transmit sound via direct vibrations of the skull. Similarly, a direct acoustic cochlear stimulation device typically utilizes a surgically-implanted mechanism to transmit sound via vibrations corresponding to sound waves to generate fluid motion in a person's inner ear. Other non-surgical vibration-based hearing aids may use similar vibration mechanisms to transmit sound via direct vibration of teeth or other cranial or facial bones.

Persons with certain forms of sensorineural hearing loss may benefit from cochlear implants. Cochlear implants may provide a person having sensorineural hearing loss with the ability to perceive sound by stimulating the person's auditory nerve via an array of electrodes implanted in the person's cochlea. An external component of the cochlear implant detects sound waves, which are converted into a series of electrical stimulation signals delivered to the implant recipient's auditory nerve via the array of electrodes. Stimulating the auditory nerve in this manner may enable the cochlear implant recipient's brain to perceive a sound.

SUMMARY

The present application discloses systems and methods for a hearing prosthesis with at least two modes of operation. In a first mode of operation, the hearing prosthesis receives a microphone input and produces an output based on the microphone input. In a second mode of operation, the hearing prosthesis may detect an accessory input signal and switch to an accessory mode. The accessory mode of operation may produce an output that is based at least in part on the accessory input signal.

Some embodiments may include detecting an accessory input signal with a detector. Responsive to detecting the accessory input signal, the hearing prosthesis may switch to an accessory operation mode. When the accessory input signal is not detected, the hearing prosthesis may operate in microphone operation mode.

A method according to one embodiment includes detecting a frequency modulated (FM) radio signal as an accessory input. The FM signal may correspond to an audio input to the audio processor. In some embodiments, the accessory input may take other forms. For example, the accessory input may be a different type of radio signal, such as amplitude modulation (AM) radio, Wi-Fi™ (IEEE 802.11), Bluetooth™ (IEEE 802.15), or the Nordic Semiconductor 2.4 GHz ShockBurst™ family of protocols. The accessory input may also be a telecoil. In some embodiments, the accessory input may be an audio cable input, such as 3.5 mm audio jack, 2.5 mm audio jack, or mobile phone adapter. In additional embodiments, the accessory input may comprise a supplemental audio microphone, or other additional input.

In the embodiments where the hearing prosthesis is operating in the second mode of operation, the hearing prosthesis may produce an output based at least in part on the accessory input signal. In some embodiments, the accessory input signal and the microphone signal may be mixed according to a amplification/attenuation to create the output signal. In other embodiments, the output signal may be based only on the accessory input signal.

In one example embodiment, a hearing impaired student in a classroom may wear the hearing prosthesis. The student's hearing prosthesis may have an FM radio receiver either attached externally, or built into the prosthesis. The teacher may wear a microphone coupled to an FM transmitter. An FM radio link between the FM transmitter and the FM radio receiver may provide a high quality audio link between the teacher and the hearing impaired student. In the example embodiment, the hearing prosthesis may detect a signal from the FM transmitter at the FM receiver, and switch to operation in an accessory mode. In the accessory mode, the hearing prosthesis may produce an output based on both (1) the signal received at the FM receiver and (2) a signal from the microphone of the hearing prosthesis. Additionally, in the accessory mode, the hearing prosthesis may attenuate the signal from the microphone of the hearing prosthesis so that the output signal applied to the prosthesis recipient is based only on the signal received over the FM radio link. If there is no audio signal received over the FM radio link, the hearing prosthesis may revert to microphone operation mode. In microphone operation mode, the hearing prosthesis may create an output based on only the signal received by the microphone.

In another example embodiment, the accessory input may be coupled to a Bluetooth™ (IEEE 802.15) or Nordic Semiconductor ShockBurst or Enhanced ShockBurst radio link. The radio link may couple the hearing prosthesis to a cellular phone via a radio frequency signal. When the cellular phone is engaged in a phone call, audio may be transmitted from the phone to the hearing prosthesis via the radio link. Upon detecting a signal via the radio link, the hearing prosthesis may switch to operate in an accessory mode. In this accessory mode, the hearing prosthesis may attenuate the signal received from the microphone of the prosthesis. Additionally, the output of the hearing prosthesis may be a combination of the audio from the radio link and the attenuated microphone signal. For example, if a prosthesis recipient of the hearing prosthesis received a phone call while driving a car, the recipient would still be able to hear ambient driving noises while on the call.

In another example embodiment, the accessory input may be a telecoil in the hearing prosthesis. The telecoil may couple the hearing prosthesis to a cellular phone with inductive (or magnetic) coupling of the baseband audio signal. In some embodiments, the telecoil in the hearing prosthesis may be able to detect an inductive (or magnetic) baseband audio signal produced by the cellular phone. During an active cellular phone call, audio may be transmitted from the phone to the hearing prosthesis via the telecoil. Upon detecting a signal via the telecoil, the hearing prosthesis may then switch to operating in an accessory mode. In this accessory mode, the hearing prosthesis may attenuate the signal received from the microphone of the prosthesis. Additionally, the output of the hearing prosthesis may be a combination of the audio from the telecoil link and the attenuated microphone signal.

Additionally, in some embodiments, the hearing prosthesis may be able to determine an incorrect accessory mode setup. The hearing prosthesis may be able to cause an alert to be issued to a recipient. The alert may be in the form of a solid or flashing light emitting diode (LED), or an indication on the screen of a separate remote-control unit for the hearing prosthesis, or other form of alert.

Additionally, in some embodiments, the hearing prosthesis may be able to determine a correct and functioning accessory mode setup. The hearing prosthesis may be able to cause an 'OK' indication to be issued to the recipient. This indication may be in the form of a solid or flashing light emitting diode (LED), or an indication on the screen of a separate remote-control unit for the hearing prosthesis, or other form of indication.

DETAILED DESCRIPTION

The following detailed description describes various features and functions of the disclosed systems and methods with reference to the accompanying figures. In the figures, similar symbols typically identify similar components, unless context dictates otherwise. The illustrative system and method embodiments described herein are not meant to be limiting. Certain aspects of the disclosed systems and methods can be arranged and combined in a wide variety of different configurations, all of which are contemplated herein.

For illustration purposes, some features and functions are described with respect to cochlear implants. However, many features and functions may be equally applicable to other types of hearing prostheses that may use accessory inputs or secondary inputs. Certain aspects of the disclosed systems, methods, and articles of manufacture could be applicable to any type of hearing prosthesis now known or later developed that can be configured to generate outputs based on one or more signals received from (1) a microphone of the prosthesis and (2) one or more accessory or secondary inputs.

1. An Example Hearing Prosthesis

Figure 1:
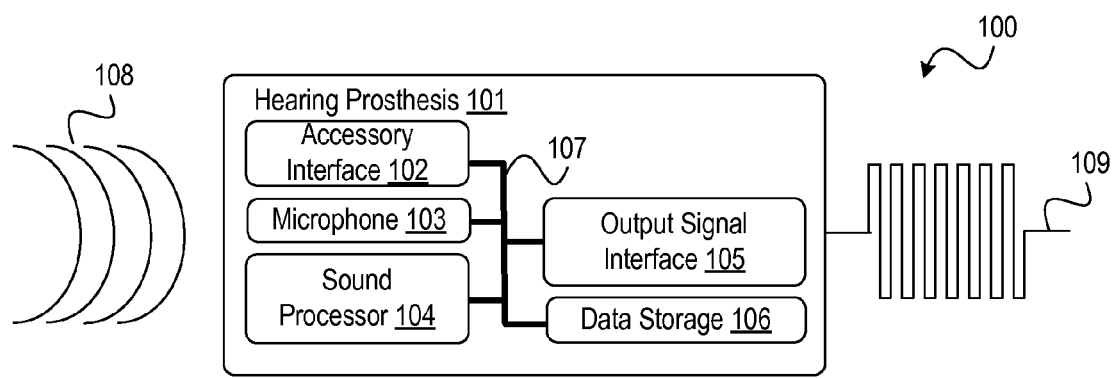
FIG. 1 shows one example of a hearing prosthesis.

FIG. 1 shows one example 100 of a hearing prosthesis 101 configured according to some embodiments of the disclosed systems, methods, and articles of manufacture. The hearing prosthesis 101 may be a cochlear implant, an acoustic hearing aid, a bone anchored hearing aid or other vibration-based hearing prosthesis, a direct acoustic stimulation device, an auditory brain stem implant, or any other type of hearing prosthesis configured to receive and process at least one accessory input signal in addition to signals from a microphone of the prosthesis.

The hearing prosthesis 101 includes an accessory interface 102, a microphone 103, a sound processor 104, an output signal interface 105, and data storage 106, all of which are connected directly or indirectly via circuitry 107. In other embodiments, the hearing prosthesis 101 may have additional or fewer components than the prosthesis shown in FIG. 1. Additionally, the components may be arranged differently than shown in FIG. 1. For example, depending on the type and design of the hearing prosthesis, the illustrated components may be enclosed within a single operational unit or distributed across multiple operational units (e.g., an external unit, an internal unit, etc.).

In embodiments where the hearing prosthesis 101 is a cochlear implant, the microphone 103 receives acoustic signals 108, and the sound processor 104 analyzes and encodes the acoustic signals 108 into a group of electrical stimulation signals 109 for application to an implant recipient's cochlea via an output signal interface 105 communicatively connected to an array of electrodes. Individual sets of electrodes in the array of electrodes are grouped into stimulation channels. Each stimulation channel has at least one working electrode (current source) and at least one reference electrode (current sink). In operation, the cochlear implant applies electrical stimulation signals to a recipient's cochlea via the stimulation channels. It is these stimulation signals that cause the recipient to experience sound sensations corresponding to the sound waves received by the microphone 103 and encoded by the processor 104.

As shown in FIG. 1, the hearing prosthesis 101 also has an accessory interface 102. The accessory interface 102 may be implemented with a radio receiver (such as frequency modulation (FM) radio, amplitude modulation (AM) radio, Wi-Fi™ (IEEE 802.11), or Bluetooth™ (IEEE 802.15)), telecoil, audio cable input (such as 3.5 mm audio jack, 2.5 mm audio jack, or mobile phone adapter), supplemental audio microphone, or other additional input. The accessory input allows a recipient to bypass a portion of the circuitry of the hearing prosthesis, which may allow the recipient to hear a high quality audio signal directly from the accessory input.

2. General Audio Processor Overview

The operation of a hearing prosthesis 101 involves receiving an audio signal and converting the received sound to a signal to cause the recipient to experience a sound sensation. For example, in a traditional hearing aid, the received sound may be converted to an amplified audio signal and applied to a recipient's outer ear. In a cochlear implant, the received sound may be converted to an electrical signal and applied to the recipient's cochlea. And in a vibration based hearing aid, the received sound may be converted to a mechanical vibration and applied to the recipient's teeth or other cranial or facial bones. The current apparatus and methods may relate to any type of hearing prosthesis and are not limited to cochlear implants.

Figure 2A:
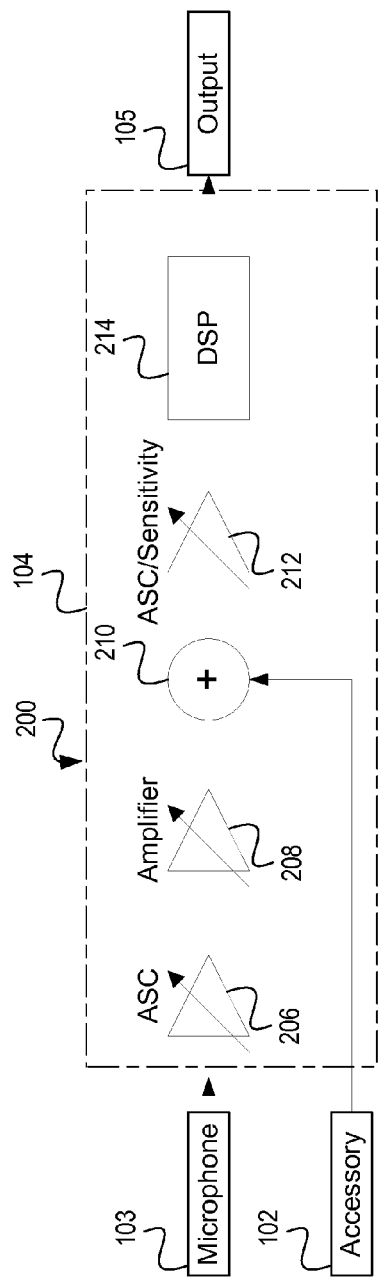
FIG. 2A is a schematic diagram illustrating one example audio processor arrangement.

FIG. 2A is a schematic diagram illustrating one example audio processor arrangement 200 where an audio processing system 104 has two inputs, a microphone input 103 and an accessory input 102, and an output 105. In many embodiments, the microphone input 103 is coupled to a microphone. However, in some embodiments, microphone input 103 may be coupled to a different audio source, such as a wired audio jack or other audio input. Additionally, the accessory input 102 may be coupled to a variety of accessories as discussed above with respect to FIG. 1. Additionally, the amplifier 208 and the DSP 214 may be coupled to an external switch. The external switch may allow a recipient to select either a microphone operation mode or accessory operation mode. However, an external switch is not required for operation as will be described herein.

Although the elements of audio processing system 104 are shown connected in a specific order, other configurations are possible. Some elements may be added or omitted depending on the specific configuration of the prosthesis.

In the example shown in FIG. 2A, the microphone input 103 may be coupled to an automatic sensitivity control (ASC) 206. The ASC 206 provides dynamic attenuation (or gain) to the signal provided by the microphone input 103. The attenuation provided by the ASC 206 may vary based on the microphone input 103 signal strength. For example, a low amplification may be provided to high level signals. Additionally, the attenuation provided by ASC 206 may be programed by an audiologist or clinician based on the needs of a patient. The ASC may be used to handle the dynamic range of input signals. For example, the ASC may increase the amplitude of a low volume signal, while attenuating the amplitude of a high volume signal.

The output of the ASC 206 may be coupled to an amplifier 208. The amplifier 208 may provide either a static gain or an attenuation to the signal output from the ASC 206 depending on the mode of operation. Additionally, in some embodiments and modes of operation, the amplifier 208 may provide a unity gain, thus providing no amplification or attenuation to the signal. The amplification/attenuation may be set by an audiologist or clinician based on the needs of a patient. An example amplification/attenuation may be 6 dB attenuation of a signal, or 12 dB amplification of a signal. Other values of the amplification/attenuation may be selected.

In some embodiments, the amplifier 208 may have two distinct amplifications/attenuations. The first amplification/attenuation may be used when the audio processing system 104 is operating in a microphone input mode. In some embodiments, the amplification/attenuation in microphone input mode may be 0 dB (unity gain) or the amplifier 208 may be bypassed completely in microphone input mode. The amplifier 208 may use a second and different amplification/attenuation when the audio processing system 104 is used in an accessory input mode. In some embodiments of the traditional example arrangement 200, operation mode is chosen by a recipient with a switch. In one example embodiment, in microphone operation mode, the amplifier 208 may provide a gain of 6 dB to the signal. In the same embodiment, in accessory operation mode, the amplifier 208 may provide an attenuation of 6 dB to the signal. Thus, in this particular example embodiment, the signal output by the amplifier 208 may vary by 12 dB depending on the mode selection.

In some embodiments, the output of amplifier 208 may be coupled to mixer 210. Mixer 210 may also receive accessory input 102. The mixer may combine the two signals to create an output signal.

In still further embodiments, the mixer and the amplifier may combine the signals in different proportions based on the type of accessory signal received at the accessory input 102. For example, the amplification/attenuation used for combining the microphone signal with the accessory signal when the accessory signal is an FM signal may be different than the amplification/attenuation used for combining the microphone signal with the accessory signal when the accessory signal is a Bluetooth™ signal. Similarly, the amplification/attenuation used for combining the microphone signal with an accessory signal from one Bluetooth™ device may be different from the amplification/attenuation used for combining the microphone signal with an accessory signal from a different Bluetooth™ device.

In some embodiments, the output of the mixer may be coupled to a second ASC amplifier. In various embodiments, the second ASC may be combined with a manual sensitivity adjustment. The second ASC and sensitivity adjustment are shown as ASC/Sensitivity amplifier 212. Although the two units are shown as one block, they may also be realized as two discrete elements. The second ASC may operate in a similar manner as ASC 206. The ASC may function to drive a smaller dynamic range on output signals as opposed to its input signals. For example, the ASC may amplify a low volume signal, while attenuating the high volume signal.

The sensitivity portion of ASC/Sensitivity amplifier 212 may be a dynamic user-controlled gain controller. In some embodiments, the sensitivity may be similar to a volume controller. The recipient may be able to control the gain of the sensitivity stage to adjust the signal level to his or her preference. For example, in a quiet environment, the recipient may want the hearing prosthesis to have a higher volume level. Conversely, in a loud environment, a recipient may wish to decrease the volume of the hearing prosthesis. Thus, the recipient may control and adjust the sensitivity level of the prosthesis as desired.

The output of the ASC/Sensitivity amplifier 212 may be coupled to a digital signal processor (DSP) 214. In one embodiment, the DSP 214 may set or control various hearing prosthesis parameters. Two parameters related to cochlear implants are the threshold level and the comfort level. Threshold levels and comfort levels may vary from recipient to recipient and from stimulation channel to stimulation channel. The threshold levels and the comfort levels determine in part how well the recipient hears and understands detected speech and/or sound.

The threshold level may correspond to the level where the recipient first identifies sound sensation. In general, the threshold level is the lowest level of stimulation current that evokes the sensation of sound for a given channel. The threshold level can often be determined by passing the recipient's hearing threshold twice using an ascending method and determining the level at which the recipient experiences sound by observing their response, such as, for example, indicating gestures in the case of adults, or observing behavioral reactions in the case of children.

The comfort level may set the maximal allowable stimulation level for each electrode channel. The comfort level may correspond to the maximum stimulation current level that feels comfortable to the recipient. In setting and establishing the comfort levels, it may be usual for an audiologist or clinician to instruct the recipient to indicate a level that is "as loud as would be comfortable for long periods" while slowly increasing the stimulation for a particular channel.

Although the terminology may be device-specific, the general purpose of threshold and comfort levels is to configure the dynamic operating range of the cochlear implant by defining the lowest stimulation levels (threshold levels) and the highest acceptable stimulation levels (comfort levels) for each stimulation channel.

The threshold levels may be mapped to an input threshold sound pressure level (T-SPL), such that sounds which are below said T-SPL level will not evoke a sensation for the recipient. This mapping allows the dynamic operating range of the cochlear implant to be matched to a dynamic range of the sound environment.

In some embodiments, the T-SPL levels may be adjusted based on the operation mode of the hearing prosthesis. For example, when the hearing prosthesis is operating in accessory mode it may be desirable to increase the T-SPL signal level. By increasing the T-SPL level when operating in accessory mode, the hearing prosthesis may suppress low-level background noise which is present on the accessory input signal. This helps improve the recipient's ability to hear the audio associated with the accessory signal. The output of the DSP 214 may be connected to output circuitry 105 of the hearing prosthesis. As described herein, the output circuitry may take various forms depending on the configuration of the audio processing system 104. For example, the output circuitry 105 may be associated with an acoustic transducer or speaker when the prosthesis is an acoustic hearing aid. Similarly, the output circuitry 105 may be associated with a bone conduction driver when the prosthesis is a vibration-based hearing prosthesis. Also, the output circuitry 105 may be associated with an array of electrodes implanted in an implant recipient's cochlea when the prosthesis is a cochlear implant.

3. Accessory Detection Audio Processing System Overview

Figure 2B:
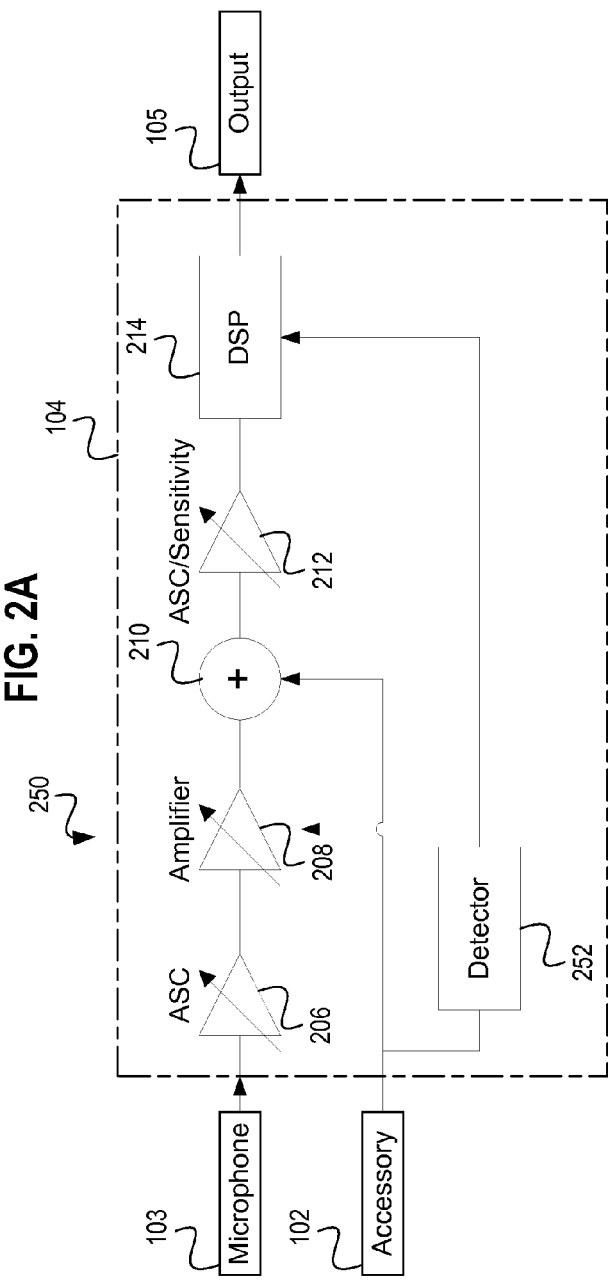
FIG. 2B is a schematic diagram illustrating an example accessory detection arrangement.

FIG. 2B is a schematic diagram illustrating an example accessory detection arrangement 250 where an audio processing system 270 has two inputs: (1) a microphone input 103 and (2) an accessory input 102. The audio processing system 270 also has an output 105 and an accessory signal detector 252. The microphone input 103, accessory input 102, ASC amplifier 206, mixer 210, ASC/Sensitivity amplifier 212, and output 105 all function similarly to how they were described with respect to FIG. 2A above.

In an example embodiment of the accessory detection arrangement 250, a detector 252 may be coupled to the accessory input 102. The detector may be configured to detect a predefined signal characteristic, and in response, generate an output signal to at least the amplifier 208 and the DSP 214. Both the amplifier 208 and the DSP 214 may have multiple modes of operation depending on the configuration of the accessory detection arrangement 250. For example, when the detector does not detect a signal from the accessory input 102, the amplifier 208 and the DSP 214 may operate in microphone input mode. However, when the detector detects a signal from the accessory input 102, the amplifier 208 and the DSP 214 may operate in an accessory input mode.

While in the accessory input mode, DSP 214 may execute a noise-suppression algorithm optimized to suppress noise signals that are specific to a specific accessory coupled to accessory input 102. For example, when an FM input accessory is coupled to accessory input 102, DSP 214 may operate with a noise-suppression algorithm designed to remove noise associated with FM signals. Different noise-suppression algorithms may be used depending on what type of accessory is coupled to accessory input 102. In another example, DSP 214 may execute an algorithm designed to enhance telephone signals for use with a telephonic accessory (e.g. Bluetooth accessory, telephone accessory, etc.). For example, if a telephone-based accessory is detected as coupled to accessory input 102, the DSP 214 may provide signal processing to increase voice clarity. One possible way to increase voice clarity is to bandpass filter the input signal to remove acoustic signals outside the human voice band. Such algorithms may have a negative impact on the microphone signal. However, in certain embodiments, optimizing the signal from the accessory input 201 takes priority. And while not in the accessory input mode (e.g., while in the microphone only mode), it may be desirable to forego execution of the optimization algorithms that have negative impact on the microphone signal.

The detector 252 may be configured to detect different types of signals presented at the accessory input 102. In some embodiments, the detector 252 may be configured to detect both the presence of an attached accessory as well as a signal provided by the accessory. For example, in some cases, an accessory may be connected but not supplying an audio signal. In this example, the detector may detect the presence of the accessory and also the lack of an audio signal from the accessory. In such a situation, it may be desirable for the hearing prosthesis to operate in the microphone operation mode and alert a recipient of a possible fault. In another example, an accessory may be connected and supplying an audio signal. In such a situation, it may be desirable for the hearing prosthesis to indicate to the recipient or carer (i.e. caretaker, audiologist, clinician, etc.) that the accessory device is functioning correctly.

Figure 3:
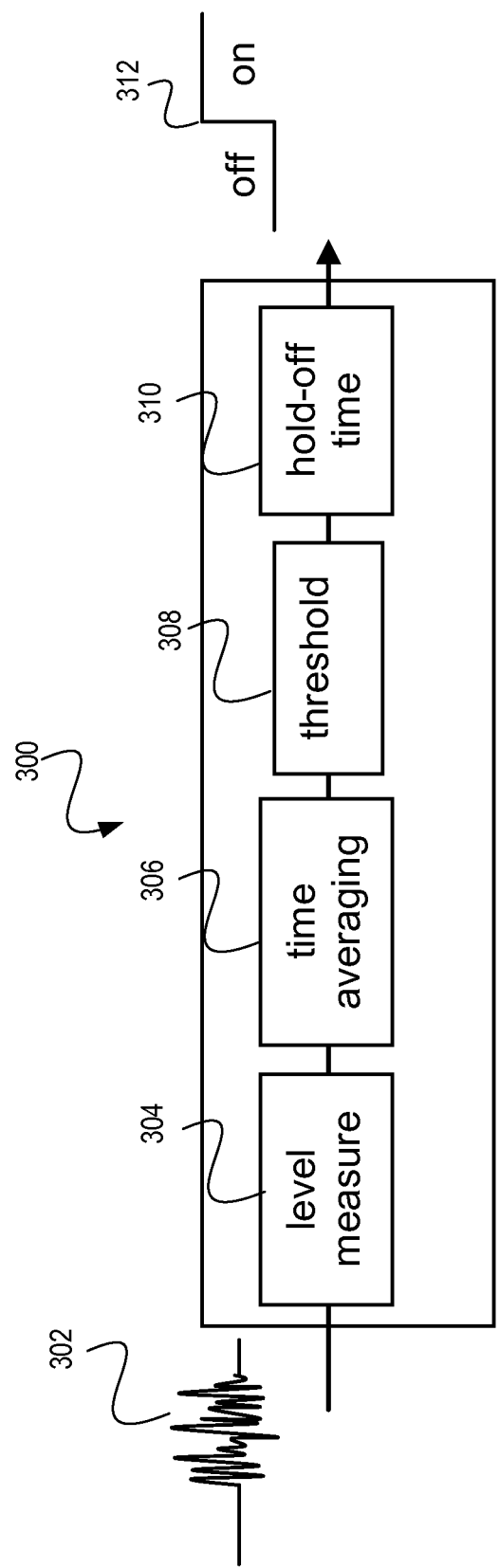
FIG. 3 an example of an audio detector.

In one example, the accessory input 102 may be the baseband output of an FM radio receiver. FIG. 3 shows an example of an audio detector. The detector 300 may receive an audio signal 302. In some embodiments, the detector may first measure a signal level present with level measure 304. The measured level may then be time averaged with the time averaging block 306. By time averaging the measured level, transient noise may be removed that may not be part of the audio signal. The time average may be compared to a threshold at block 308. The threshold level may be chosen to detect any real audio signal. For example, it may be desirable to set the threshold to a level that will ignore low signal level ambient radio noise. The hold-off time 310 will stop the detector from turning itself off too quickly, for example during gaps in speech. In one example embodiment, the hold-off time may be set to something in the order of 30 seconds. The output of the hold-off time block 310 may be a digital value 312. The low, 'off', position may correspond to no input audio signal, and the high, 'on', position may correspond to the presence of an input audio signal. This output square wave 312 of the detector may be the output of the detector and coupled to the amplifier 208 and DSP 214 as shown in FIG. 2B.

CHART 1

| | Traditional Prosthesis | | | Prosthesis with Accessory Signal Detection | | | |
| --- | --- | --- | --- | --- | --- | --- | --- |
| Scenario | Mic Signal | Accessory Signal | T-SPL Level | Mic Signal | Accessory Signal | T-SPL Level | Notification |
| Acessory Operation | Attenuated | Present | increased | Attenuated | Present | increased | off |
| Microphone only Operation | Full | N/A | nominal | Full | N/A | nominal | off |

CHART 1-continued

| | Traditional Prosthesis | | | Prosthesis with Accessory Signal Detection | | | |
| --- | --- | --- | --- | --- | --- | --- | --- |
| Scenario | Mic Signal | Accessory Signal | T-SPL Level | Mic Signal | Accessory Signal | T-SPL Level | Notification |
| FM receiver incorrectly tuned | Attenuated | Present | increased | Full | N/A | nominal | on |
| FM receiver left attached when not in use | Attenuated | Present | increased | Full | N/A | nominal | on |

Chart 1 shows the difference in operation between (1) a traditional hearing prosthesis and (2) a hearing prosthesis with the accessory signal detection in four different operating scenarios. The first scenario shows the operation of the hearing prostheses in an accessory operation mode. The second scenario shows the operation of the hearing prostheses in microphone-only operation mode. The third scenario shows the operation of the hearing prostheses in accessory mode, where the accessory is an FM receiver tuned to an incorrect channel. The fourth scenario shows the operation of the hearing prostheses in accessory mode, where the accessory is an FM receiver tuned to a channel with no radio transmission.

The first scenario shown is the accessory operation mode. In this operation mode, a traditional prosthesis may have a switch in a position indicating accessory operation mode. When operating a traditional hearing prosthesis in the accessory mode, the output signal from the hearing prosthesis may include (1) a signal received from the microphone that has been attenuated based on an amplification/attenuation in the amplifier 208 and (2) a signal received from the accessory. Chart 1 shows the Accessory Signal is "present" as part of the output signal. Additionally, in accessory operation mode, the T-SPL level may be set to an "increased" value. Increasing the T-SPL level may decrease the overall dynamic range of the hearing prosthesis, but it increases the lower limit of the output.

In accessory operation mode, a prosthesis with accessory signal detection may operate similarly to a traditional prosthesis as long as an accessory signal is present. Like the traditional prosthesis, the output signal from the hearing prosthesis with accessory detection may include (1) a signal received from the microphone that has been attenuated based on an amplification/attenuation in the amplifier 208 and (2) a signal received from the accessory. Additionally, in accessory operation mode the T-SPL level may be set to an "increased" value.

In additional embodiments, the traditional prosthesis or the hearing prosthesis with accessory signal detection may not have a switch. In the embodiments without a switch, the hearing prosthesis may automatically switch to operate in accessory mode when the detector detects an accessory. By automatically switching the hearing prosthesis to accessory operation mode only when an accessory is present, the recipient of the hearing prosthesis may not have to actively switch his or her hearing prosthesis to accessory mode, thus providing a better user experience.

In microphone only operation mode, the traditional prosthesis and the prosthesis with accessory signal detection may also operate similarly. In microphone only operation, the output signal from the hearing prosthesis with accessory detection may include a signal received from the microphone. In microphone operation mode, the output signal typically has not been attenuated based on an amplification/attenuation in the amplifier 208. Additionally, the output does not contain any signal received from an accessory. In microphone operation mode the T-SPL level may be set to the "nominal" value. The T-SPL may be set lower in microphone operation mode to allow for a wider dynamic range of outputs from the hearing prosthesis.

Chart 1 also shows the advantages of a prosthesis with accessory signal detection in situations when an FM receiver is tuned to an incorrect channel or when the FM receiver is tuned to a channel with no radio transmission. The two scenarios are simply examples; there are other situations where accessory signal detection may provide an advantage over a traditional hearing prosthesis. In both of these scenarios shown in Chart 1, the traditional prosthesis may behave the same way as if it was operating in accessory mode. For example, the output signal from the traditional hearing prosthesis may include (1) a signal received from the microphone that has been attenuated based on an amplification/attenuation in the amplifier 208 and (2) a signal received from the accessory. Additionally, the T-SPL level may be set to an "increased" value. However, since no signal would be provided by the accessory in the third and fourth scenarios, the user experience of a traditional prosthesis may be impaired. To the recipient, they would simply notice the microphone signal has been undesirably attenuated.

A prosthesis with accessory signal detection may improve the recipient's user experience as compared to a traditional prosthesis in scenarios where an accessory is connected but does not provide an accessory signal to the hearing prosthesis. In such a situation, the prosthesis with accessory signal detection will operate as if it was in microphone operation mode. As shown in Chart 1, the output signal from the hearing prosthesis with accessory detection includes a signal received from the microphone and the output signal has not been attenuated based on an amplification/attenuation in the amplifier 208. Additionally, the output does not contain any signal received from an accessory. Furthermore, the T-SPL level may be set to the "nominal" value. In some embodiments, the prosthesis with accessory signal detection may also create a notification such as visual or audible notification. The notification may allow a recipient to know there is a fault in the system that may need correcting.

Thus, the systems and methods disclosed herein may allow a hearing prosthesis to detect a fault mode and responsively alert a recipient of the fault while attempting to mitigate the effect of the fault. Additionally, the disclosed systems and methods may allow the hearing prosthesis to switch between microphone operation mode and accessory operation mode without the recipient having to toggle a switch.

Figure 4:
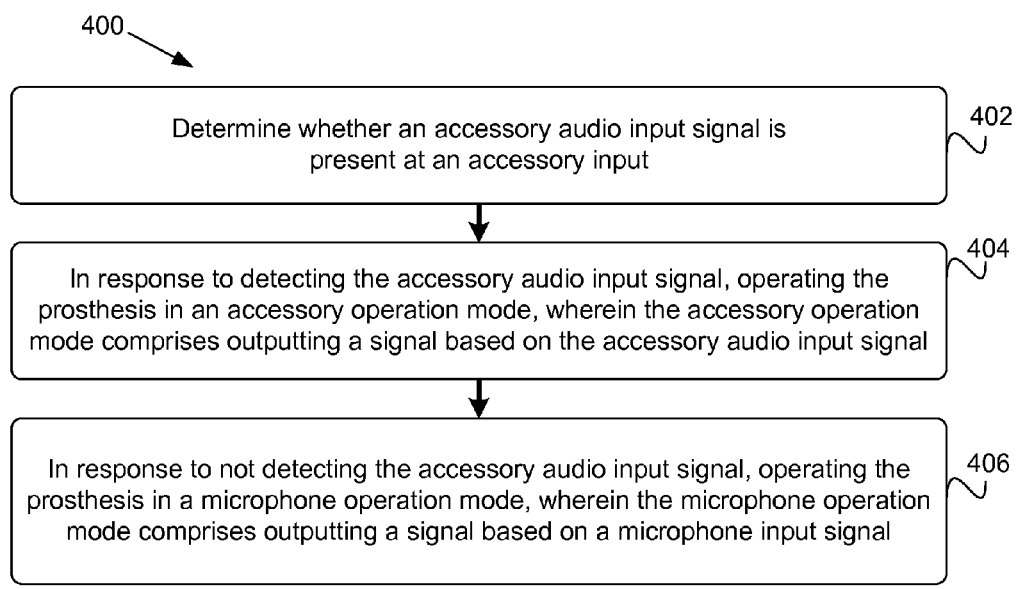
FIG. 4 is a flow diagram of one embodiment of an algorithm for use with the accessory detection methods.

FIG. 4 is a flow diagram of one embodiment of the accessory detection methods presented herein. Some examples of method 400 may be performed by the example accessory detection arrangement 250 show in FIG. 2B. Although the blocks are illustrated in a sequential order, these blocks may also be performed in parallel, and/or in a different order than those described herein. Also, the various blocks may be combined into fewer blocks, divided into additional blocks, and/or eliminated based upon the desired implementation.

Method 400 may begin at block 402, where the prosthesis detects whether an accessory input signal is present at an accessory input. The accessory input signal may be configured to cause the hearing prosthesis to switch to operating in the accessory mode. In some examples of block 402, a detector is configured to detect an accessory input signal. The accessory input signal may be a signal from the accessory corresponding to a sound. In some embodiments, the accessory input signal may be a down converted RF signal (e.g., FM, WiFi™, Bluetooth™, etc.). In other embodiments, the accessory input signal may be a baseband audio signal. In some additional embodiments, the accessory input signal may be a radio signal containing audio data.

Block 402 may be followed by block 404, where, in response to detecting the accessory audio input signal, the hearing prosthesis switches to operate in an accessory mode. In the accessory operation mode, the hearing prosthesis may output a signal based on the accessory audio input signal. In some examples of block 404, the hearing prosthesis may switch to an accessory operation mode upon detection of the accessory input signal. The accessory operation mode may comprise adjusting parameters of the hearing prosthesis as described herein. For example, in accessory operation mode, an amplifier may attenuate the signal from the microphone based on a amplification/attenuation. For embodiments where the prosthesis is a cochlear implant, operating in the accessory operation mode may also include increasing T-SPL levels for one or more stimulation channels. Additionally, when operating in accessory operation mode, the hearing prosthesis may generate an output based on the accessory audio input signal.

Block 404 may be followed by block 406, where if an accessory input signal is not detected, the prosthesis may be switched to operating in a microphone mode. The microphone operation mode comprises the hearing prosthesis outputting a signal based on a microphone input signal. In some examples of block 406, the hearing prosthesis may operate in a microphone operation mode when an accessory audio input signal is not detected. The microphone operation mode may comprise adjusting parameters of the hearing prosthesis as described herein. When the prosthesis is operating in the microphone operation mode, the microphone input may not be attenuated. In microphone operation mode, the hearing prosthesis may generate an output based on the microphone input signal.

Figure 5:
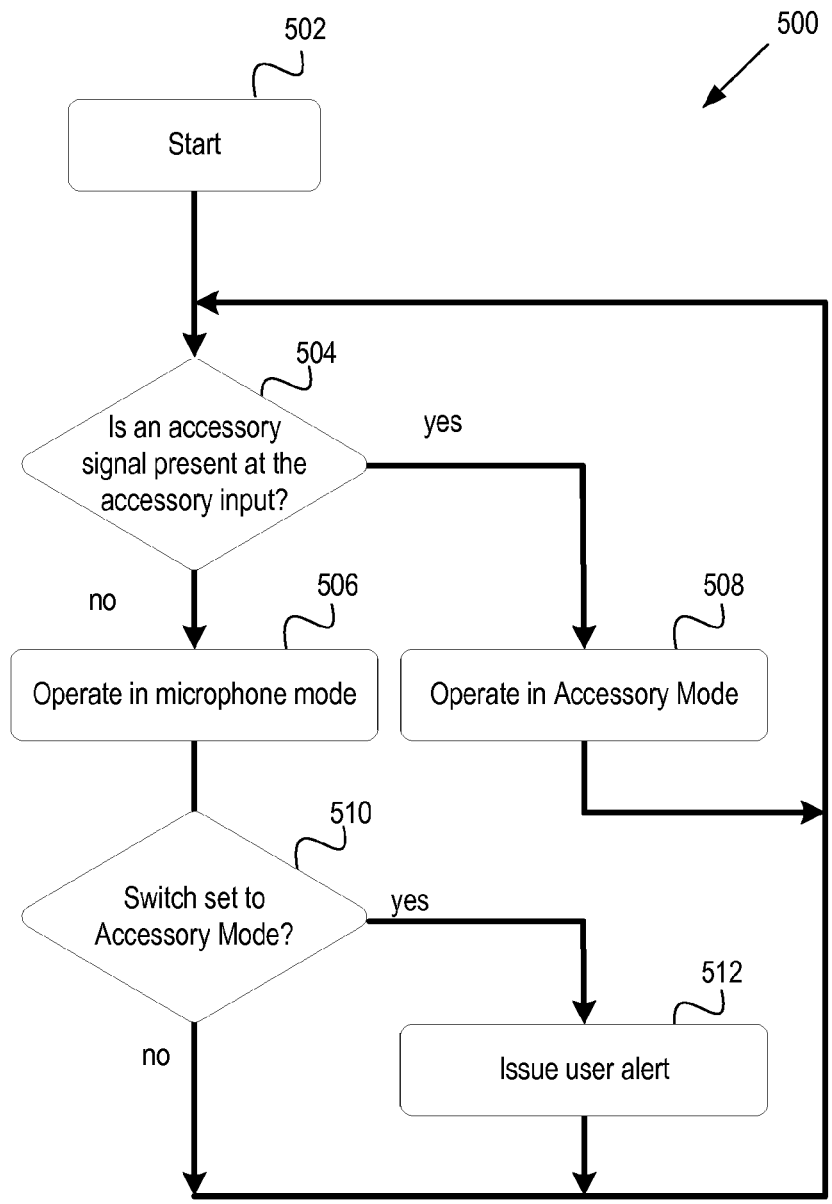
FIG. 5 is a flow diagram of one embodiment of an algorithm for use with the accessory detection methods.

FIG. 5 is a flow diagram of one embodiment of an algorithm for use with the accessory detection methods presented herein. Although the blocks are illustrated in a sequential order, these blocks may also be performed in parallel, and/or in a different order than those described herein. Also, the various blocks may be combined into fewer blocks, divided into additional blocks, and/or eliminated based upon the desired implementation.

The algorithm 500 may start at block 503. At block 504 a determination is made as to whether an accessory signal is present at the accessory input. The accessory may be coupled to a variety of different accessories as described herein. A detector may be similar to the example FM radio detector described with respect to FIG. 3. The detector does not have to be the same as the detector shown in FIG. 3; any detection circuit may be used. For example, the detector circuit may be built into a radio chipset. If the accessory is a Bluetooth™ receiver, the Bluetooth™ chipset may have a built in detection circuit. Thus, the decode chipset may be able to provide signal detection as well.

If an accessory signal is detected at block 504, then the algorithm 500 may proceed to block 508 where the hearing prosthesis is switched to operate in an accessory mode. In accessory option mode, the output of the hearing prosthesis may be based at least in part on the accessory input signal. But if an accessory signal is not detected at block 504, then the algorithm 500 may proceed to block 506 where the hearing prosthesis may be switched to operate in a microphone mode. In microphone operation mode, the output of the hearing prosthesis may be based at least in part on the microphone input signal.

In some embodiments of algorithm 500, after switching the prosthesis to operate in microphone mode, the algorithm 500 may check to see the setting of an accessory mode indicator at block 510. If the accessory mode indicator is set to 'no' for accessory mode, the algorithm may operate normally and produce an output of the hearing prosthesis based at least in part on the microphone input signal.

In some embodiments, the switch may be a user-controllable switch. In other embodiments, the switch may be not be user-controllable, but instead, the switch may be controlled by a detector configured to detect a connected accessory. In some embodiments, the detector may be configured to detect a physical connection from an accessory (e.g., a plug). In other embodiments, the detector may be configured to detect an RF signal from an accessory as described herein.

Regardless of whether the switch is a user-controllable switch or a detector-controlled switch, if the switch is set to indicate operation in accessory mode, the algorithm may issue a user alert at block 512. An alert issued in at block 512 may take the form of playing a tone, an illumination of a light or LED, or other user alert. For embodiments where the switch is a user-controllable switch, the alert may indicate that the switch is in the incorrect position. For embodiments where the switch is a detector-controlled switch, the alert may indicate that the accessory is not functioning correctly. The accessory may be connected (physically connected via a cable or connected via an RF link), but there may be no signal on the link between the accessory and the prosthesis. In such a situation, the output of the hearing prosthesis may still be based at least in part on the microphone input signal. However, the alert may allow the user to know the accessory mode is not working correctly or was incorrectly selected.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:
1. An apparatus comprising:
an accessory input configured to receive a first input signal from an accessory;
a detector coupled to the accessory input and configured to determine whether the first input signal includes audio data;
a microphone input configured to receive a second input signal from a microphone; and
signal processing circuitry including:
a first automatic sensitivity control (ASC) coupled to the microphone input, and configured to apply attenuation or gain to the second input signal, and to provide a first output signal, at an output of the first ASC, based on the attenuation or gain applied to the second input signal;

a mixer coupled to the output of the first ASC and to the accessory input, and configured to provide a second output signal, at an output of the mixer, based on at least one of the first input signal or the first output signal;

a second ASC coupled to the output of the mixer, and configured to apply attenuation or gain to the second output signal, and to provide a third output signal based on the attenuation or gain applied to the second output signal; and a processor coupled to the output of the detector and the third output signal, and configured to, in response to, the detector determining that the first input signal includes audio data, process the first input signal and generate a fourth output signal based at least in part on the processed first input signal.

2. The apparatus of claim 1, wherein the first ASC is configured to apply dynamic attenuation or dynamic gain to the second input signal based on a signal strength of the second input signal, and wherein the second ASC is configured to apply dynamic attenuation or dynamic gain to the second output signal based on a signal strength of the second output signal.

3. The apparatus of claim 1, wherein the signal processing circuitry further includes an amplifier coupled between the first ASC and the mixer, and wherein the amplifier is configured to apply attenuation to the second input signal in response to the detector determining that the first input signal includes audio data.

4. The apparatus of claim 3, wherein the mixer is configured to provide, in response to the detector determining that the first input signal includes audio data, the second output signal based on the first input signal and the attenuated second input signal.

5. The apparatus of claim 1, wherein the processor is further configured to execute a noise-suppression algorithm to process the first input signal in response to the detector determining that the first input signal includes audio data.

6. The apparatus of claim 5, wherein the processor is further configured to choose, based on a type of accessory from which the first input signal was received, the noise-suppression algorithm from a set of noise-suppression algorithms.

7. The apparatus of claim 1, wherein the detector is configured to measure a signal level of the first input signal, time average the measured signal level, and compare the time average with a threshold level for detecting data corresponding to the audio signal.

8. The apparatus of claim 1, further comprising alert generation circuitry configured to generate an error indication in response to the detector determining that the first input signal does not include audio data.

9. The apparatus of claim 8, wherein the alert generation circuitry is configured to generate, in response to the detector determining that the first input signal does include audio data, an indication that the accessory is functioning correctly.

10. An apparatus comprising:
an accessory input configured to receive a first input signal from an accessory;
a detector coupled to the accessory input and configured to determine whether the first input signal includes audio data;
a microphone input configured to receive a second input signal from a microphone; and
signal processing circuitry coupled to the accessory input and to the microphone input, and configured to:
apply attenuation or gain to the second input signal and provide a first output signal based on the attenuation or gain applied to the second input signal;
mix the first input signal and the first output signal to provide a second output signal;
apply attenuation or gain to the second output signal and provide a third output signal based on the attenuation or gain applied to the second output signal; and
in response to the detector determining that the first input signal includes audio data, process the first input signal and generate a fourth output signal based at least in part on the processed first input signal.

11. The apparatus of claim 10, wherein the signal processing circuitry is configured to apply dynamic attenuation or dynamic gain to the second input signal based on a signal strength of the second input signal, and to apply dynamic attenuation or dynamic gain to the second output signal based on a signal strength of the second output signal.

12. The apparatus of claim 10, wherein the signal processing circuitry is further configured to apply attenuation to the first output signal in response to the detector determining that the first input signal includes audio data.

13. The apparatus of claim 12, wherein the signal processing circuitry is configured to mix, in response to the detector determining that the first input signal includes audio data, the first input signal and the attenuated first output signal to provide the second output signal.

14. The apparatus of claim 10, wherein the signal processing circuitry is further configured to execute a noise-suppression algorithm to process the first input signal in response to the detector determining that the first input signal includes audio data.

15. The apparatus of claim 14, wherein the signal processing circuitry is further configured to choose, based on a type of accessory from which the first input signal was received, the noise-suppression algorithm from a set of noise-suppression algorithms.

16. The apparatus of claim 10, wherein the detector is configured to measure a signal level of the first input signal, time average the measured signal level, and compare the time average with a threshold level for detecting data corresponding to the audio signal.

17. The apparatus of claim 10, further comprising alert generation circuitry configured to generate an error indication in response to the detector determining that the first input signal does not include audio data.

18. The apparatus of claim 17, wherein the alert generation circuitry is configured to generate, in response to the detector determining that the first input signal does include audio data, an indication that the accessory is functioning correctly.

* * * * *